United States Patent [19]

Brooks

[11] 4,021,197

[45] May 3, 1977

[54] HAIR STYLIST'S ACCESSORY

[76] Inventor: Lawrence L. Brooks, 4415 Lancewood, Irvine, Calif. 92715

[22] Filed: June 21, 1976

[21] Appl. No.: 698,041

[52] U.S. Cl. ............................ 21/84; 21/77; 21/83; 21/91; 132/79 R; 206/207; 206/234; 206/373; 206/526

[51] Int. Cl.² ................ A61L 7/00; A45D 27/46; B65D 81/28

[58] Field of Search .............. 21/83, 77, 84, 91, 88, 21/DIG. 4; 206/207, 208, 209, 209.1, 234, 373, 526; 132/79 R

[56] References Cited

UNITED STATES PATENTS

| | | | |
|---|---|---|---|
| 3,093,242 | 6/1963 | Huyck et al. | 21/91 UX |
| 3,292,993 | 12/1966 | Musso | 21/83 |
| 3,342,544 | 9/1967 | Curiel | 21/83 |
| 3,460,899 | 8/1969 | Miller | 21/83 |
| 3,476,506 | 11/1969 | Anderson et al. | 21/83 X |
| 3,498,742 | 3/1970 | Long | 21/91 |
| 3,554,688 | 1/1971 | Cassidy | 21/91 |

*Primary Examiner*—Barry S. Richman
*Attorney, Agent, or Firm*—William C. Babcock

[57] ABSTRACT

A portable hair stylist's accessory adapted to receive and hold one or more pairs of shears, combs and the like in individual pouches until needed, and the shears and combs when stored in the pouches and prior to being used, being subjected to a pressurized disinfectant to kill bacteria and germs that may be lodged thereon. The pressurized disinfectant is disposed in a container concealed within the accessory and is released therefrom as required by a manually operated valve to flow through passages defined in the accessory to the pouches holding the shears, combs and the like.

4 Claims, 3 Drawing Figures

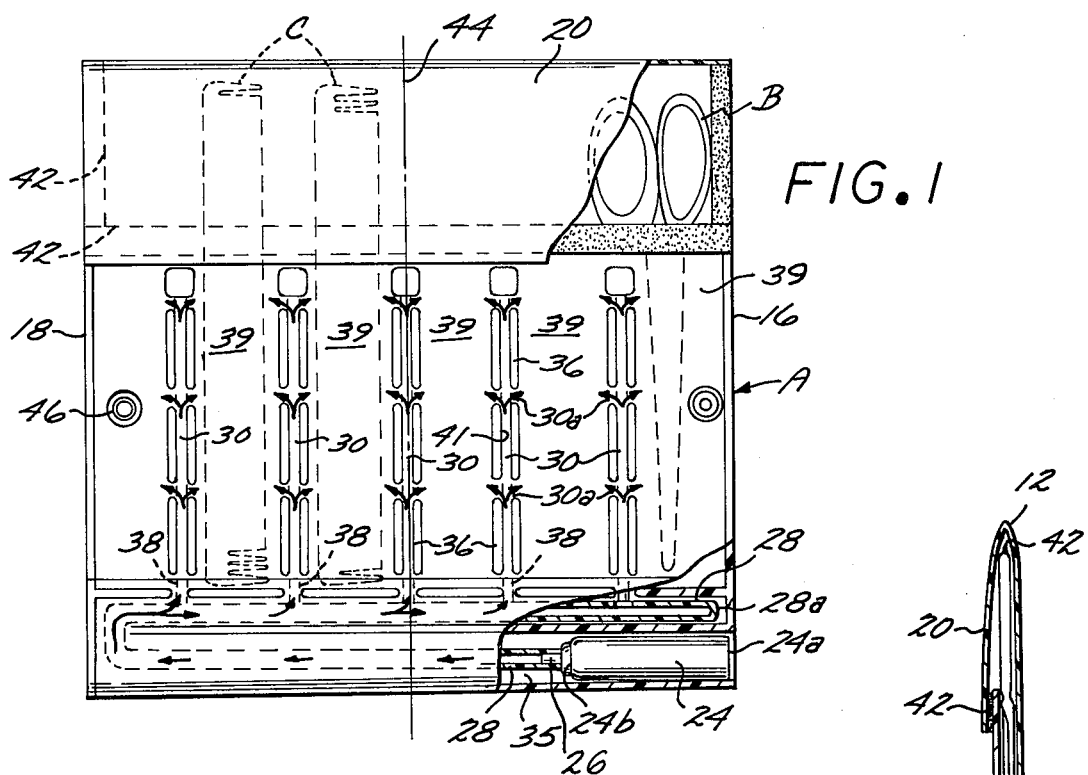
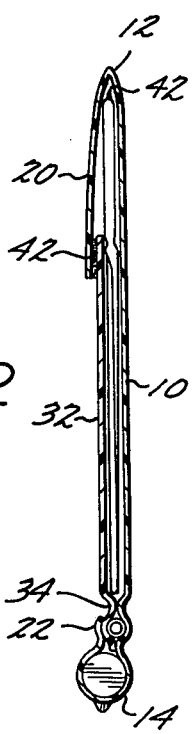
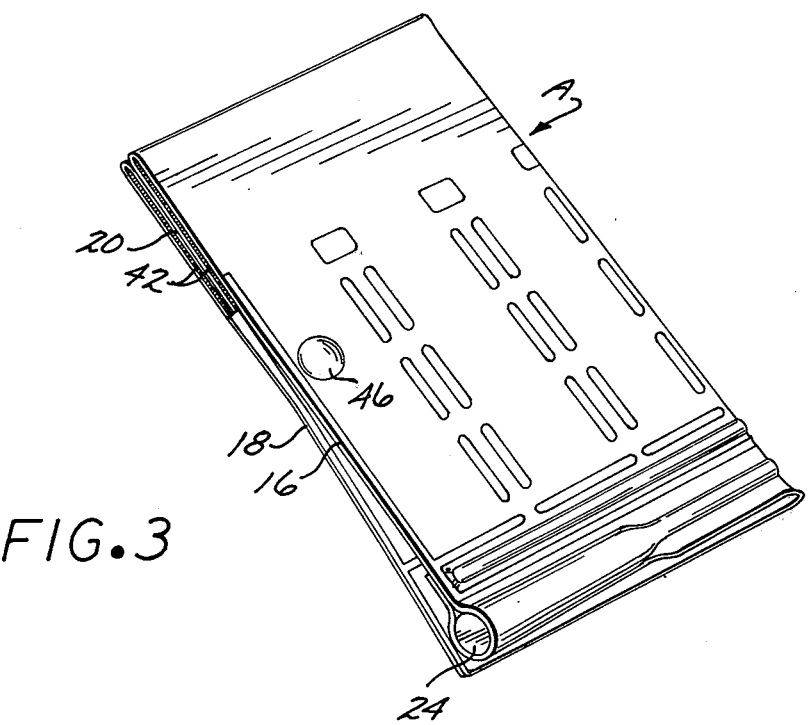

HAIR STYLIST'S ACCESSORY

BACKGROUND OF THE INVENTION

1. Field of the Invention

A portable hair stylist's accessory.

2. Description of the Prior Art

A hair stylist's shears, combs and like accessories are of the utmost importance to him in his profession, and it is not ony desirable that they be maintained in a predetermined relationship in a portable container in which they are readily accessible, but that they be disinfected prior to use by the hair stylist.

In the past, combs after use are immersed in a liquid disinfectant to kill bacteria and other germs that may adhere thereto. Such a means is unsatisfactory in that the insertion and removal of the combs from a body of liquid disinfectant is time-consuming, is inconvenient, and requires accessories so immersed to be dried prior to usage.

A major object of the present invention is to provide a portable device in which a hair stylist's shears, combs, and the like may be stored in a predetermined relationship, and the shears, combs and the like when so disposed in the invention being subjected to a disinfecting action to eliminate the necessity of immersing these implements in a liquid disinfectant prior to the use of the implements.

Another object of the invention is to provide a portable device that is simple and easy to use, is compact and light in weight, and one that eliminates substantially the operational disadvantages of disinfecting a hair stylist's implement by being immersed in a liquid disinfectant prior to being used.

SUMMARY OF THE INVENTION

The present hair stylist's accessory for maintaining shears, combs and the like in a sterile condition prior to the use thereof includes a first rectangular sheet of pliable material that has a top edge, bottom edge and first and second side edges. The sheet has first and second oppositely disposed side surfaces. A rectangular first flap of pliable material extends downwardly from the top edge of the sheet over a first part of the first surface. A second rectangular flap of pliable material extends upwardly from the bottom edge over a second portion of the first surface of the first sheet.

A cylindrical container is provided that holds a quantity of pressurized disinfectant, with this container having first and second ends, and the first end having a normally closed spring-loaded valve mounted thereon. A first tube is connected to the discharge end of the spring-loaded valve, and this first tube having a free closed end. A number of spaced parallel second tubes extend outwardly from the first tube and normal thereto, with the second tubes being in communication with the interior of the first tube. The second tubes have a number of longitudinally spaced sets of apertures therein.

A second sheet of pliable material overlies a third portion of the first side of the first sheet and is situated intermediate the first and second portions previously mentioned with the edge areas of the first and second flaps extending over the second sheet. The second flap is so bonded to the second sheet, and the second sheet so bonded to the first sheet that the second flap and second sheet cooperate to define an elongate compartment in which the container, valve and first tube may be disposed. The second sheet is bonded to the first sheet in such a manner that the first and second sheets cooperate to define a number of pouches that are normally disposed to the compartment previously mentioned, and in which pouches the hair stylist's shears and combs may be removably disposed when inserted therein through openings in the upper portions of the pouches adjacent the first flap. The pouches have passage means defined therebetween in which the second tubes are disposed, with the second sets of apertures in the second tubes in communication with the interior of the pouches.

Third means such as a zipper, strips of Velcro or the like, are provided for removably and sealingly securing free edge areas of the first flap to the first part of the first surface and an edge area of the second sheet most adjacent the first flap to cooperate with the interior of the pouches to define a confined space in which the shears and combs are disposed in positions to be subjected to the pressurized disinfectant when the container in which the disinfectant is stored is moved longitudinally towards the spring loaded valve to open the latter and allow the disinfectant to flow through the first and second tubes into the above-described confined space.

BRIEF DESCRIPTION OF THE DRAWINGS

FIG. 1 is a side elevational view of the hair stylist's accessory, with a portion of the device illustrated being broken away to show the interior structure thereof;

FIG. 2 is a cross sectional view of the device illustrated in FIG. 1 taken on the line 2—2 thereof;

FIG. 3 is a perspective view of the device illustrated in FIG. 1 in a folded configuration suitable for being carried by a hair stylist.

DESCRIPTION OF THE PREFERRED EMBODIMENT

The hair stylist's accessory A as may best be seen in FIG. 1 is adapted to hold at least one pair of shears B and a number of combs C. The accessory A is defined by a first rectangular sheet 10 of a pliable material such as one of the numerous plastic materials commercially available, and the sheet 10 having a top edge 12 and bottom edge 14. The sheet 10 includes first and second side edges 16 and 18.

The top edge 12 of the first sheet 10 as may best be seen in FIG. 2 develops into a first rectangular downwardly extending flap 20. The bottom edge 14 of the first sheet 10 as may also be seen in FIG. 2 develops into a second rectangular upwardly extending flap 22. The accessory A also includes a cylindrical container 24 that has first and second ends 24a annd 24b. The second end 24b has a normally closed spring loaded valve 26 mounted thereon, which valve when in the open position permits a disinfectant that is pressurized with aerosol or the like within the container 24 to discharge therefrom. The disinfectant may be any one of the commercially available materials used for this purpose at the present time, that kills bacteria or germs upon coming in contact therewith. A first tube 28 is connected to the discharge end of the spring loaded valve 26, with this first tube being illustrated in FIG. 1 as of U-shaped configuration, and the tube having a free end 28a that is closed. A number of second tubes 30 that are parallel and laterally spaced are provided that are in communication with the interior of the first tube 28 and secured to the latter. Each second tube 30, as can be seen in FIG. 1, has a number of longitudinally spaced sets of apertures 30a formed therein. The first and second tubes are formed from a pliable material such as a polymerized resin but with the material having sufficient resiliency that the tubes at all times tend to maintain open passages within the interior thereof. A second rectangular sheet 32 is provided that is also formed from a pliable material such as a polymerized resin, and the second sheet overlying an intermediately disposed portion of the first sheet 10 as can be seen in FIGS. 1 and 2. First bonding means 34 which may be an adhesive, heat seal, or the like, secures the second flap 22 to the second sheet 32 and the second sheet 32 to the first sheet 10 so that they cooperate to define an elongate compartment as may be seen in FIG. 1 in which the container 24, valve 26, and the first tube 28 are disposed. The first tube 28 has sufficient longitudinal rigidity as to prevent longitudinal movement of valve 26 towards the tube 28. Thus, when container 24 is moved longitudinally towards the valve 26, the valve is opened to permit pressurized disinfectant to flow from container 24 into first and second tubes 28 and 30.

Second bonding means 36, which may be an adhesive, heat seal, or the like, secure spaced segments of the second sheet 32 to the first sheet 10 in such a manner that the first and second sheets cooperate to define a number of elongate pouches 39 in which shears B and combs C may be disposed as shown in FIG. 1. The second bonding means 36 also so secures the second sheet 32 to first sheet 10 in such a manner that elongate confined spaces 41 are defined between pouches 39 in which the second tubes 30 are disposed. The sets of apertures 30a are in communication with the interior of the pouches 39 due to transverse passages 38 that are formed by adjacent portions of first sheet 10 and second sheet 32 that are not bonded to one another.

The three interior marginal edge surfaces of the first flap 20 have strips 42 of Velcro or other sealing means secured thereto which may sealingly and removably engage like strips 42 on the surface of first sheet 10 adjacent first and second side edges 16 and 18 and a strip on the upper exterior edge area of second sheet 32. When first flap 20 is in the sealed downwardly extending position shown in FIG. 2, the pressurized disinfectant discharged into the interior of the pouches 39 cannot escape from the accessory A, and all portions of the shears B and comb C disposed within the accessory are rendered sterile due to contact with the disinfectant. The disinfectant is discharged into the interior of the pouches 39 as a mist.

The first and second sheets 10 and 32 preferably have a vertically extending folding line 44 formed therein, to permit the accessory A to be disposed in the folded configuration shown in FIG. 3. If desired, pairs of snaps 46 may be disposed on the interior portions of the second sheets 32 to hold the accessory A in the folded condition shown in FIG. 3.

The use and operation of the invention has been explained previously in detail and need not be repeated.

I claim:

1. A portable hair stylist's accessory for maintaining shears, combs and the like in a sterile condition prior to the use thereof, said accessory comprising:
   a. a first rectangular sheet of pliable material that has a top edge, bottom edge and first and second side edges, said sheet having first and second oppositely disposed side surfaces, a rectangular flap of pliable material that extends from said top edge over a first part of said first surface, and a second rectangular flap of pliable material that extends from said bottom edge over a second portion of said first surface of said first sheet;
   b. a cylindrical container that holds a quantity of pressurized disinfectant, said container having first and second ends;
   c. normally closed spring-loaded valve means on said first end of said container, with said valve opening when said container is moved longitudinally towards said valve means;
   d. a first tube connected to said spring-loaded valve means, said first tube having a first closed end;
   e. a plurality of spaced parallel second tubes normally disposed to said first tube and in communication with the interior thereof, said second tubes having a plurality of longitudinally spaced sets of apertures therein;
   f. a second sheet of pliable material that overlies a third portion of said first side of said first sheet intermediate said first and second portions, and edge areas of said first and second flaps extending over said second sheet;
   g. first means so bonding said second flap to said second sheet and said second sheet to said first sheet that said second flap and second sheet cooperate to define an elongate compartment in which said container, valve means and first tube is disposed;
   h. second means so bonding said second sheet to said first sheet that said first and second sheets cooperate to define a plurality of pouches normally disposed to said compartment and in which pouches said shears and combs may be removably disposed, when inserted therein through an opening in said pouches adjacent said first flap, and said pouches having passage means defined therebetween in which said second tubes are disposed with said sets of apertures in communication with the interiors of said pouches; and
   i. third means for removably and sealingly securing free edge areas of said first flap to said first part of said first surface and an edge area of said second sheet most adjacent said first flap to cooperate with the interiors of said pouches to define a confined space in which said shears and combs are disposed in positions to be subjected to said pressurized disinfectant when said container is moved longitudinally towards said spring loaded valve means.

2. An accessory as defined in claim 1 in which said first means are elongate edge areas of said second flap that are heat sealed to said first sheet and to said second sheet.

3. An accessory as defined in claim 1 in which said second means are elongate spaced areas of said second sheet that are heat sealed to said first sheet to define said pouches and passages.

4. An accessory as defined in claim 1 in which said third means are an engaging strip on the free interior marginal edge surface of said first flap that can sealingly engage aligned engageable strips on the adjacent surfaces of said first sheet and said second sheet when said first flap is in a position to seal said opening in said pouches.

* * * * *